United States Patent [19]

Matsuzaki et al.

[11] Patent Number: 5,532,305

[45] Date of Patent: Jul. 2, 1996

[54] CONTROLLED RELEASE PREPARATION FOR BIOACTIVE SUBSTANCES

[75] Inventors: Fumiaki Matsuzaki; Toshio Yanaki, both of Yokohama; Michihiro Yamaguchi, Sagamihara, all of Japan

[73] Assignee: Shiseido Company Ltd., Tokyo, Japan

[21] Appl. No.: 280,736

[22] Filed: Jul. 26, 1994

[30] Foreign Application Priority Data

Jul. 26, 1993 [JP] Japan .................................. 5-224920

[51] Int. Cl.⁶ .................................................. A61K 47/00
[52] U.S. Cl. ................ 525/54.2; 424/78.08; 424/78.31; 424/422; 424/423; 424/425; 424/487; 424/488; 523/105; 523/113; 524/27

[58] Field of Search ................. 525/54.2; 424/78.08, 424/78.31, 422, 423, 425, 487, 488; 523/105, 113; 524/27; 536/55.1

[56] References Cited

U.S. PATENT DOCUMENTS

| 4,767,463 | 8/1988 | Brode et al. ........................... 106/162 |
| 5,143,724 | 9/1992 | Leschiner et al. .................... 424/78.08 |
| 5,334,640 | 8/1994 | Desai et al. ........................... 424/488 |

*Primary Examiner*—Nathan M. Nutter
*Attorney, Agent, or Firm*—Townsend & Banta

[57] ABSTRACT

To provide a base suitable for a controlled release preparation and the controlled release preparation. A bioactive substance(s) is introduced in a poly-ion complex of hyaluronic acid and a cationic polyacrylic acid derivative(s).

18 Claims, 7 Drawing Sheets

CONTROLLED RELEASE PREPARATION FOR BIOACTIVE SUBSTANCES

FIELD OF THE INVENTION

This invention relates in general to a poly-ion complex of hyaluronic acid and a cationic polyacrylic acid derivative(s), a carrier for a preparation which contains this poly-ion complex, and a controlled release preparation which utilizes this carrier. In particular, this invention relates to a controlled release preparation for implantation which controls the drug release independent of the pH of the part of the living body where it is administered, and thus is effective for drugs which require frequently repeated administration when venoclysis or localized administration is adopted.

DESCRIPTION OF RELATED ART

Controlled release preparations control the release of a medicine and adjust the absorption rate once the medicine has been administered in a living body. This type of preparations has been investigated for a considerable period of time. For example, a method which coats the drug with various films and a method in which the drug is contained in a matrix of wax or polymer have been known.

It is an object of the present invention to provide a preparation which allows the adjustment of the starting time of the drug release and the duration of the release. For example, a preparation which starts the drug release one or more days after administration and maintains the release for as long as 5 days or more, would be preferable in terms of a reduction in the number of administrations. However, with conventional preparations, the effect was insufficient and/or the process of adjustment was complicated. For a controlled release preparation utilizing a poly-ion complex, a controlled release type carrier utilizing chitin and/or chitosan and carboxyvinyl polymer has been proposed. However, this has a shortcoming in that it is hard to secure the procurement of the raw material since it uses a natural substance(s) as the raw material. In addition, the effect starts after approximately 3 hours after the administration and does not last for even a day; consequently, adjustment of the effect is rather limited.

As can been seen from the description above, development of a carrier has been desired which uses readily obtainable starting materials and is easily adjustable and safe, while providing sufficient controlled release, adjustable starting time of the release, and a long duration of drug release.

SUMMARY OF THE INVENTION

The present invention is based on the discovery that by using as a carrier a poly-ion complex of hyaluronic acid and cationic polyacrylic acid derivative(s), it is possible to easily adjust and control release and to maintain the release of active components for several days or longer without disintegration of the formulation.

In particular, the present invention provides:

1) A poly-ion complex of hyaluronic acid and cationic polyacrylic acid derivative(s).

2) A carrier for a preparation which contains a poly-ion complex of hyaluronic acid and cationic polyacrylic acid derivative(s).

3) A controlled release preparation which comprises a poly-ion complex of hyaluronic acid and cationic polyacrylic acid derivative(s), bioactive substance(s), and carrier thereof.

4) A controlled release preparation as described in 3) above, wherein the bioactive substance is noscapine-HCl.

5) A controlled release preparation as described in 3) above, wherein the bioactive substance is indomethacin.

DETAILED DESCRIPTION OF THE INVENTION

The bioactive substances used in the present invention can be any bioactive substance which normally requires frequent administration in order to maintain the effective concentration in the bloodstream, or an effective local concentration. Examples of such bioactive substances are noscapine-HCl and indomethacin.

The blend ratio of the bioactive substances is normally in the range of 0.01–50 wt. %, depending on the particular drug used. However, it is also possible to blend a bioactive substance with a blend ratio above or below this range.

Hyaluronic acid is a type of saccharic acid. According to the present invention, both natural hyaluronic acid and a synthetic product of gene engineering can be used.

In the present invention, specific examples of suitable cationic polyacrylic acid derivative(s) is EUDRAGIT E and EUDRAGIT RS (from Rohm Pharma, Germany), of which Eudragit E is particularly preferred. "EUDRAGIT E" is a copolymer, cationic in character, based on dimethylaminoethyl methacrylate and neunral methyacrylic acid esters having the formula:

$$\ldots -CH_2-\underset{\underset{O}{\underset{|}{\overset{|}{C=O}}}}{\overset{CH_3}{\underset{|}{C}}}-CH_2-\underset{\underset{OR}{\underset{|}{C=O}}}{\overset{CH_3}{\underset{|}{C}}}- \ldots$$

$$\underset{CH_2-N<\overset{CH_3}{\underset{CH_3}{}}}{\overset{|}{CH_2}}$$

wherein R=CH$_3$ or C$_4$H$_9$. The mean molecular weight of the copolymer is about 150,000.

"EUDRAGIT RS" are copolymers synthesized from acrylic and methacrylic acid esters with a low content of quaternary ammonium groups having the formula:

wherein $R_1$=H or $CH_3$ and $R_2$=$CH_3$ or $C_2H_5$. In this copolymer the molar ratio of the ammonium groups to the remaining neutral (meth) acrylic acid esters is preferably 1:20, and the mean molecular weight is preferably 150,000. In the present invention, these cationic polyacrylic acid derivatives can be used independently or two or more can be used in combination.

By mixing the bioactive substance and the poly-ion complex of hyaluronic acid and a cationic polyacrylic acid derivative mentioned above, a preparation of the present invention can be obtained. Each component is preferably thoroughly crashed and prepared as a powder having a small particle size. Specifically, the particle size can be 500 micrometers or less, preferably between 300 micrometers and 10 micrometers, more preferably 200 micrometers or less. For crushing, a conventional crusher can be used.

The poly-ion complex of hyaluronic acid and cationic polyacrylic acid derivative(s) containing a bioactive substance is suitable for use in implantation. However, it can also be used for conventional methods of administration such as oral administration, intestinal administration and percutaneous administration. The preparation of the present invention can be used alone or with disintegration control agents, stabilizers, antioxidants, wetting agents, binders, lubricants, etc. These preparations can be prepared in the form of tablets, pills, capsules, liquid, ointment, etc.

EXAMPLES

The present invention is described in detail below by referring to examples. It must be understood that the present invention is not limited to these examples but includes variations and modifications implemented at our company.

Example 1

Preparation of a poly-ion complex of hyaluronic acid and EUDRAGIT E:

100 g of a 2% aqueous solution of hyaluronic acid and 100 g of a 2% aqueous solution of EUDRAGIT E are mixed and brought into reaction for 2 hours at room temperature while agitated. The reaction product(s) is recovered by means of centrifugal separation at 3000 rpm for 10 minutes and vacuum-dried to obtain a poly-ion complex of hyaluronic acid and EUDRAGIT E.

Figure 1:
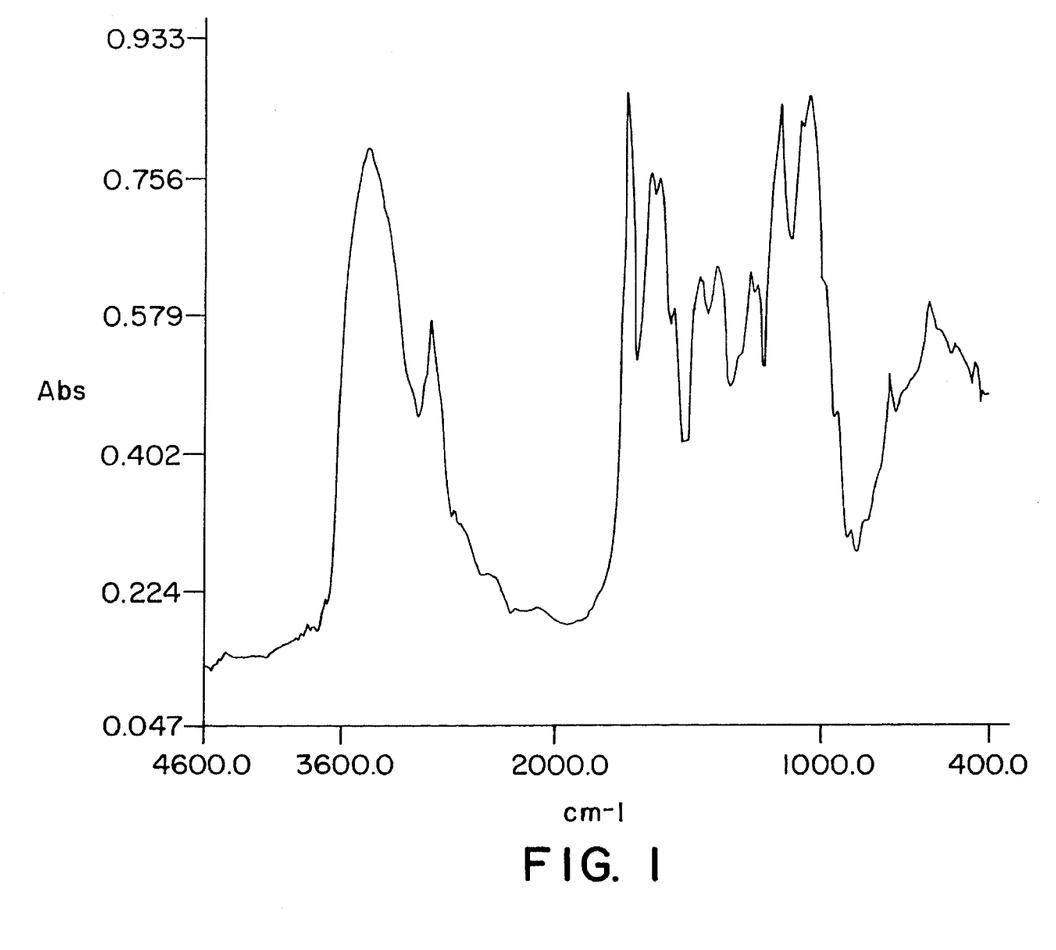
FIG. 1 is an IR chart of a poly-ion complex of hyaluronic acid and EUDRAGIT E.

The solid obtained is crushed and classified to prepare powder with a particle size of 150 micrometers. The IR spectrum of the poly-ion complex of hyaluronic acid and EUDRAGIT E thus obtained is shown in FIG. 1.

Figure 2:
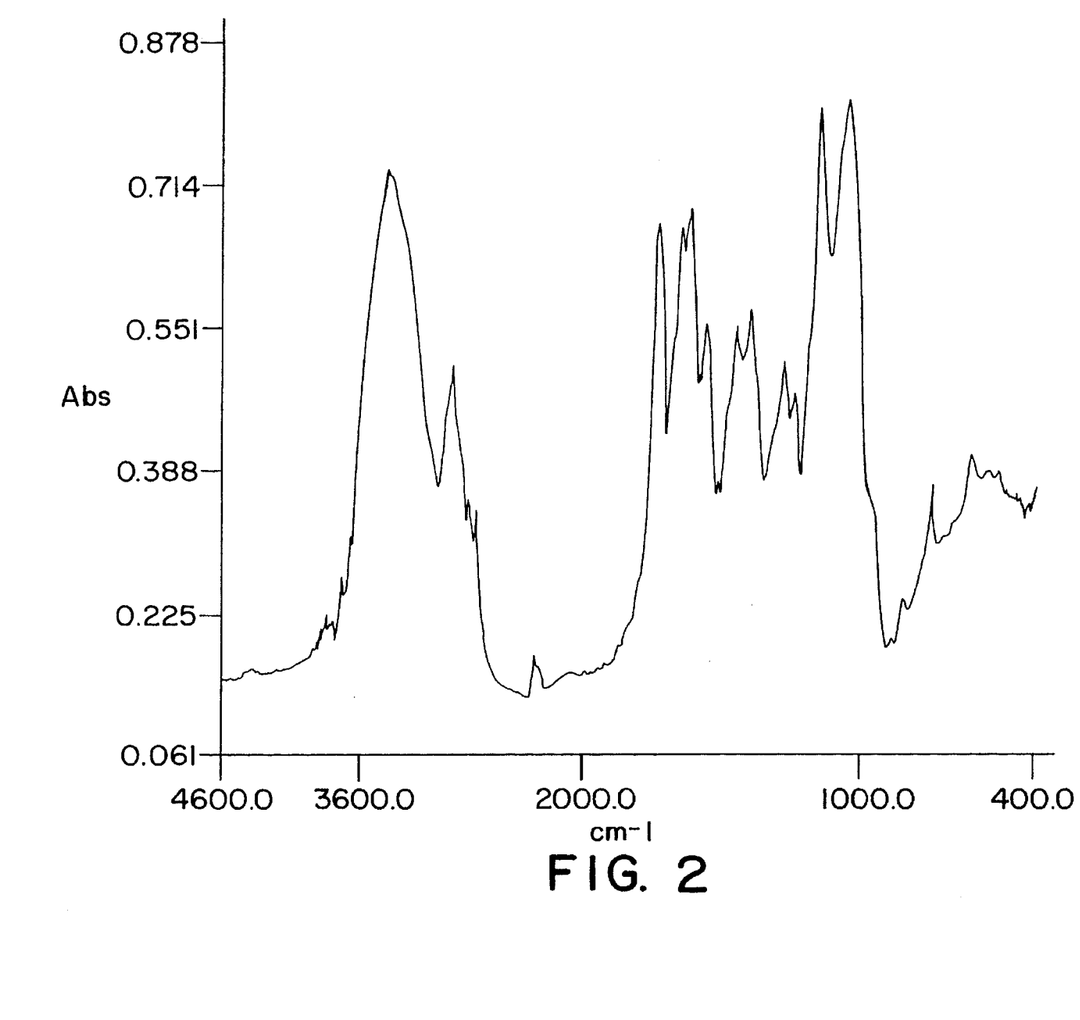
FIG. 2 is an IR chart of an equal-amount mixture of hyaluronic acid and EUDRAGIT E.
Figure 3:
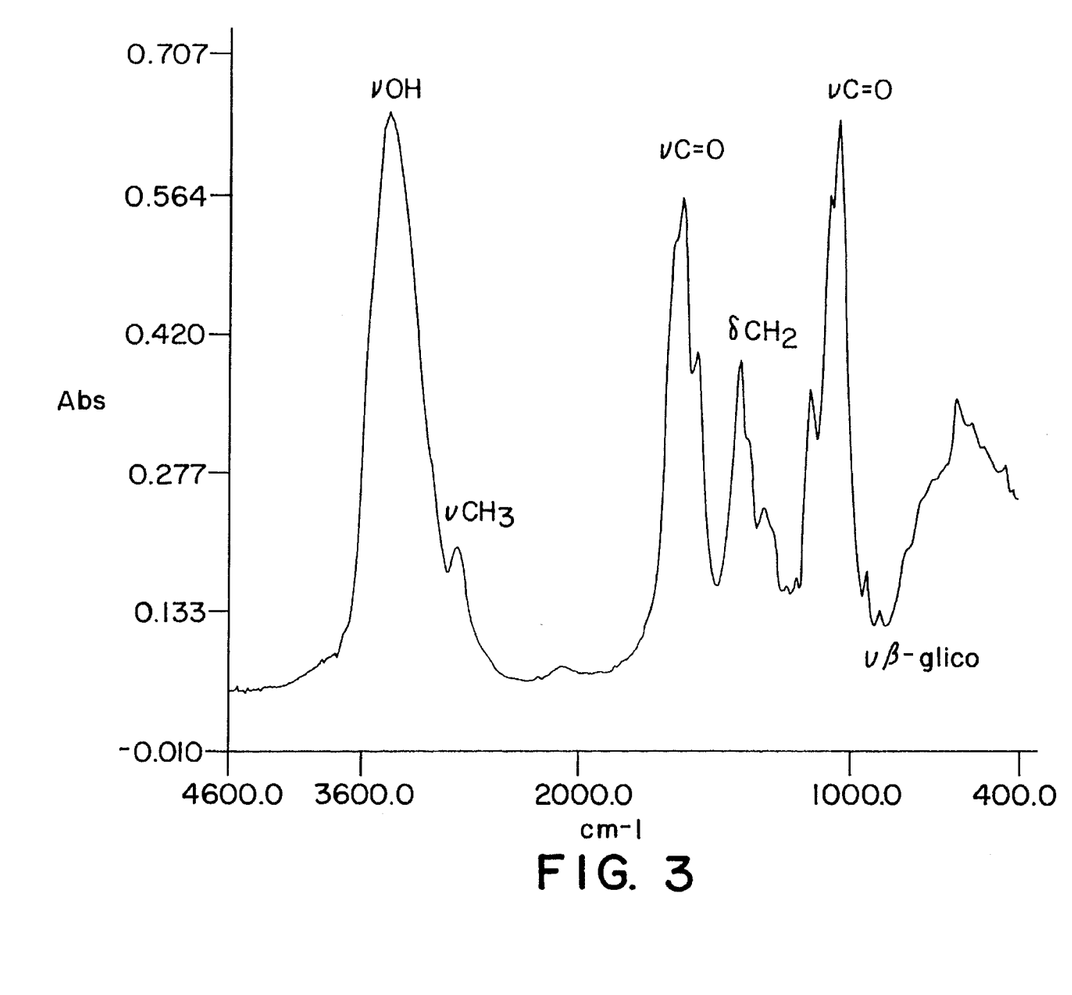
FIG. 3 is an IR chart of hyaluronic acid.
Figure 4:
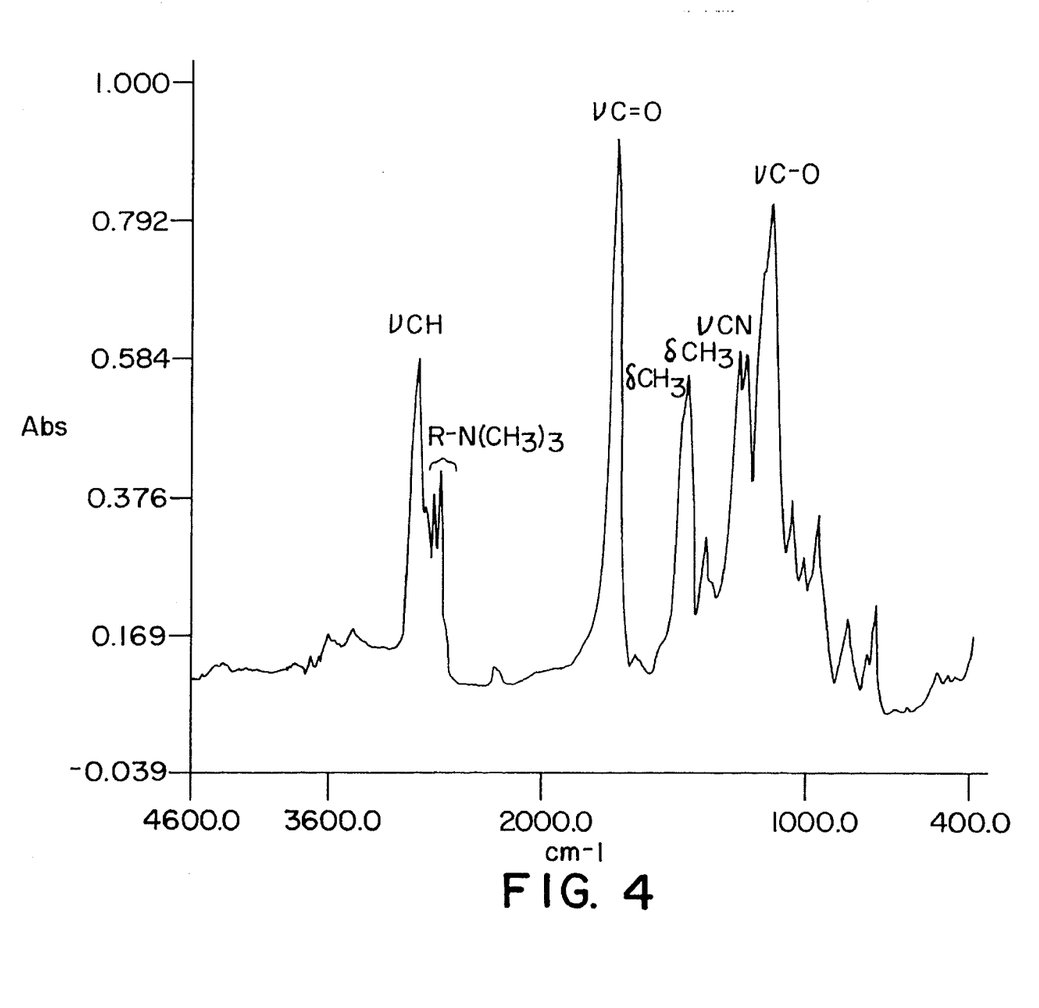
FIG. 4 is an IR chart of EUDRAGIT E.

For reference, the IR spectrum of an equal-amount mixture of hyaluronic acid and Eudragit E is shown in FIG. 2, the IR spectrum of hyaluronic acid is shown in FIG. 3, and the IR spectrum of EUDRAGIT E is shown in FIG. 4.

By comparing these IR charts, it was confirmed that the poly-ion complex of hyaluronic acid and EUDRAGIT E according to the present invention was not a mere mixture but a reaction product.

Example 2

Preparation of the controlled release preparation 0.18 g of the poly-ion complex of hyaluronic acid and EUDRAGIT E obtained in Example 1 and 0.02 g of noscapine-HCl were mixed and a flat tablet with a diameter of 13 mm was prepared by using a KBr tablet moulding device (150 kg, 1 minute) for IR spectrum measurement. The tablet weighed 0.2 g.

Reference Example 1

For comparison, a sample prepared by adding and mixing 0.02 g of noscapine-HCl to 0.09 g of EUDRAGIT E and 0.09 g of hyaluronic acid, classified into a particle size of 150 micrometers or less, a sample prepared by adding and mixing 0.02 g of noscapine-HCl to 0.18 g of hyaluronic acid, classified into a particle size of 150 micrometers or less, and a sample prepared by adding and mixing 0.02 g of noscapine-HCl to 0.18 g of EUDRAGIT E, classified into a particle size of 150 micrometers or less were made into tablets under the same conditions.

Example 3

Drug Release Test I

A tablet of the poly-ion complex of hyaluronic acid and EUDRAGIT E containing noscapine-HCl, prepared in Example 2, was immersed in 50 ml of a second solution (pH 6.8) and agitated with an agitator (100 rpm). Test solutions, 0.5 ml each, were sampled at different times and the amount of dissolved noscapine was determined using high speed liquid chromatography.

For a comparative example, the tablets prepared in Reference Example 1 were used. The drug concentration for each specimen was 10%.

Figure 5:
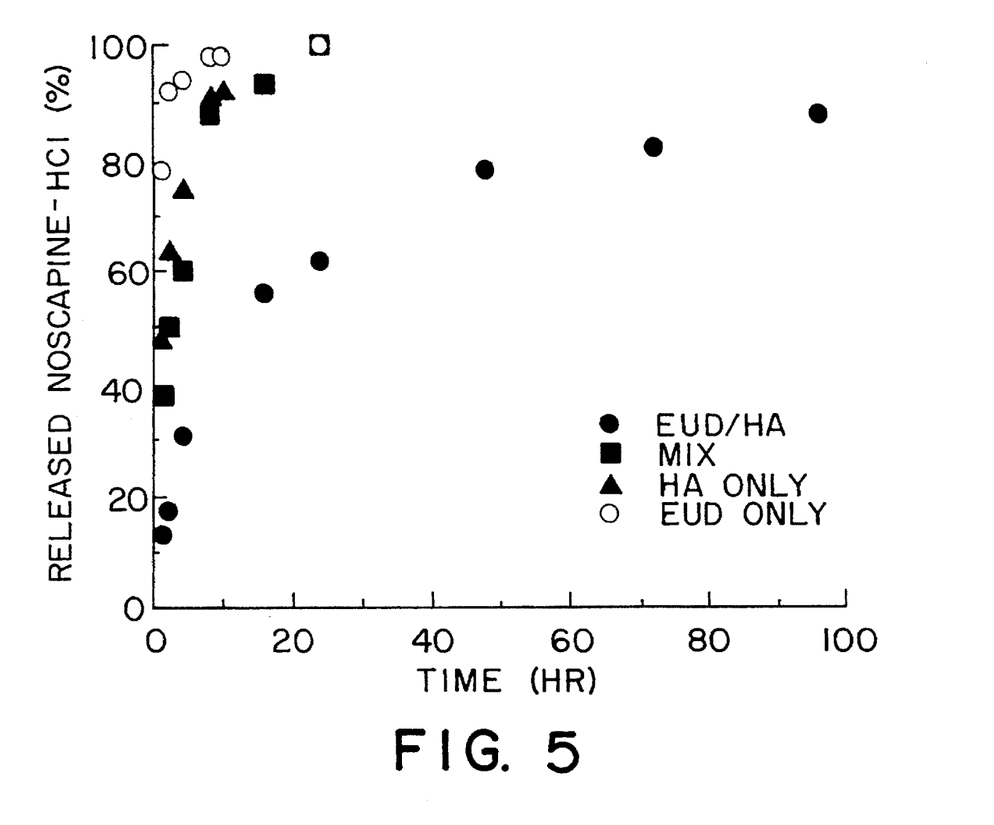
FIG. 5 shows the results of the time dependent release test for noscapine-HCl.

The results are shown in FIG. 5. In the figure, filled circles indicate the time dependent release of noscapine for the product of the present invention (EDU/HA), filled squares for the mixture of hyaluronic acid and EUDRAGIT E (MIX), filled triangles for hyaluronic acid only (HA-only), and empty circles for EUDRAGIT E only (EDU-only).

The results show that the product of the present invention releases the drug steadily for a long time, indicating excellent controlled release effect.

Example 4

Drug Release Test II 0.19 g of the poly-ion complex obtained in Example 1 and 0.01 g of indomethacin were mixed and made into a tablet in the same manner as in Example 2, then immersed in 100 ml of the first solution (buffer solution: pH 1.2) or the second solution (buffer solution: pH 6.8). The amount of dissolved indomethacin was determined by high speed liquid chromatography.

Figure 6:
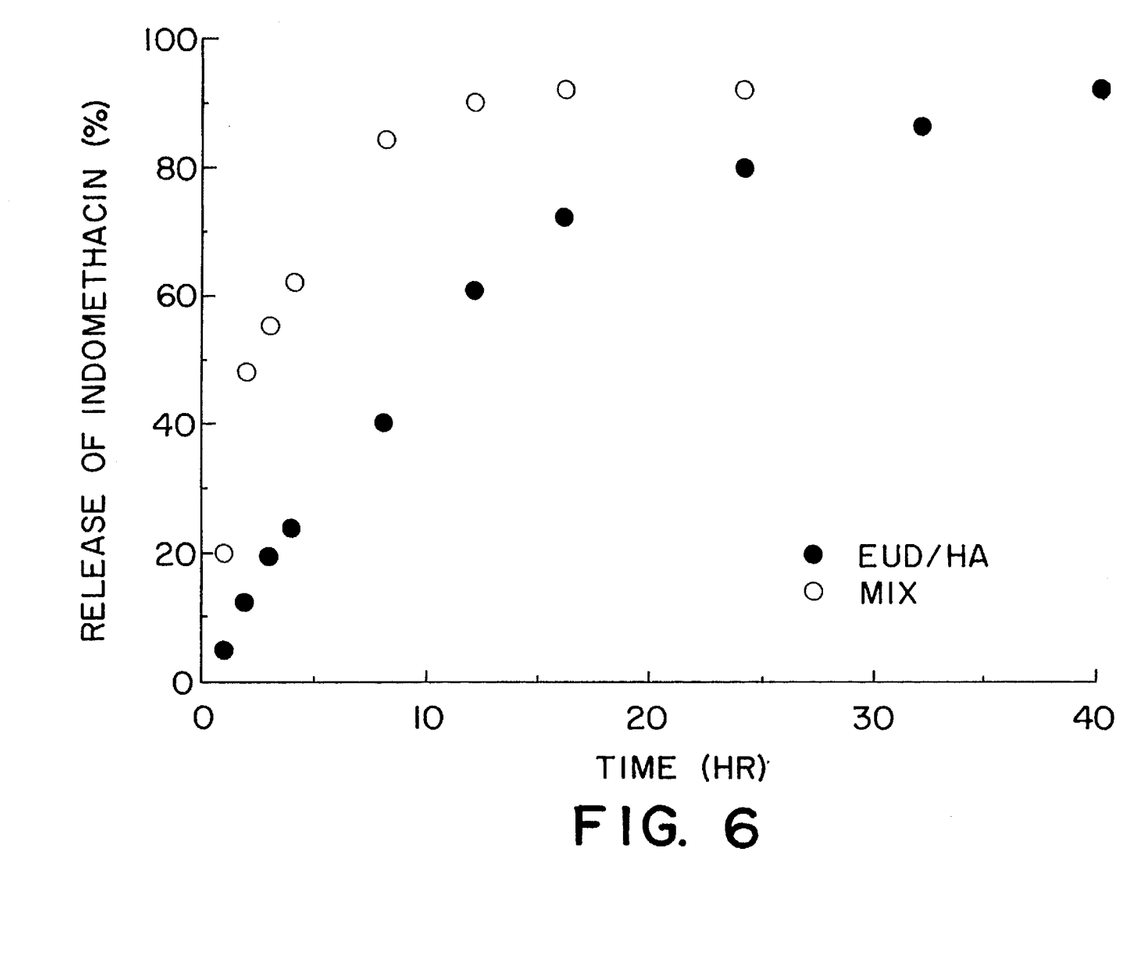
FIG. 6 shows the results of the time dependent release test for indomethacin using the first solution(buffer solution pH 1.2).
Figure 7:
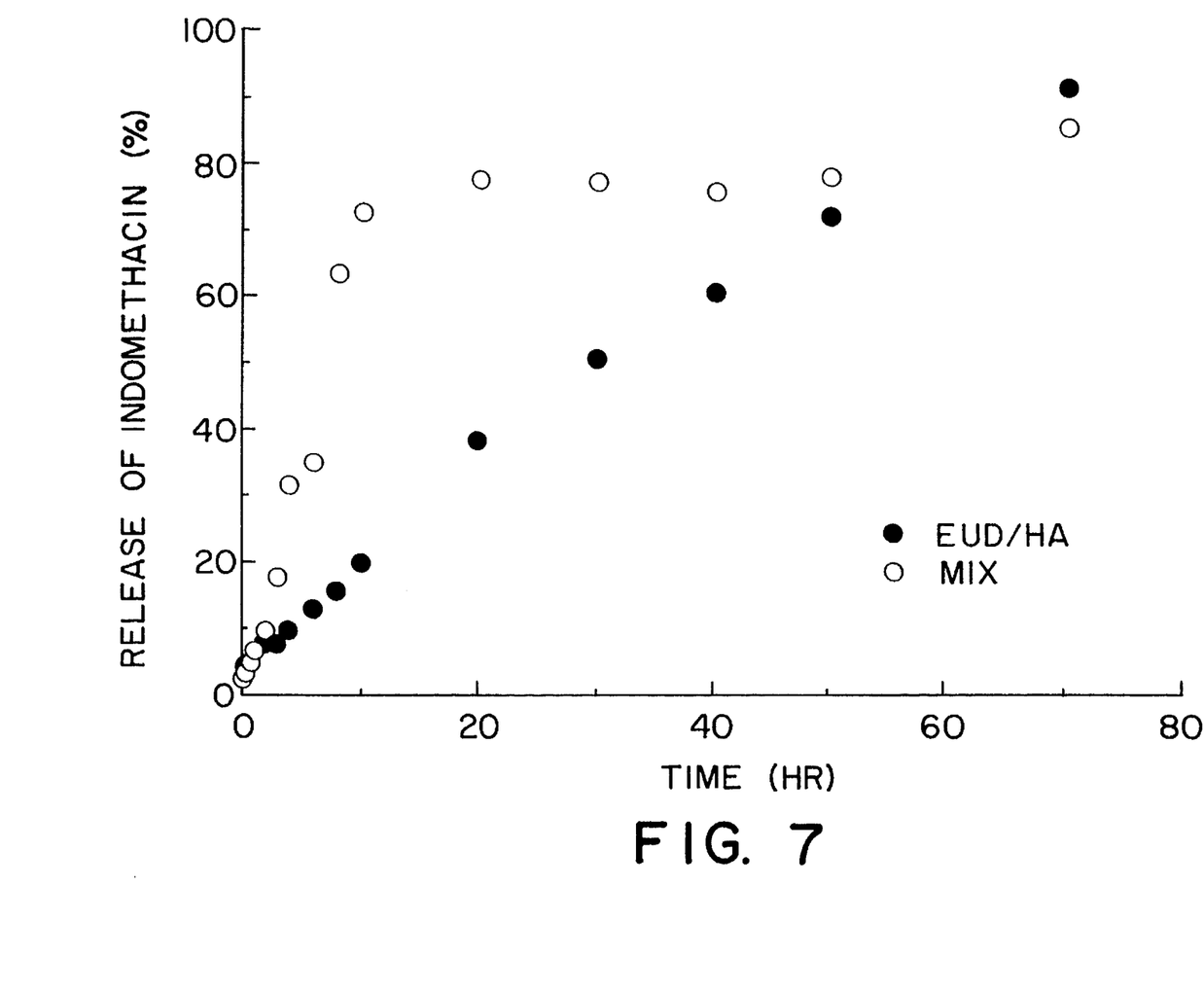
FIG. 7 shows the results of the time dependent release test for indomethacin using the second solution(buffer solution pH 6.8).

For a comparative example, a sample was prepared by adding and mixing 0.01 g of indomethacin to 0.095 g of EUDRAGIT E and 0.095 g of hyaluronic acid, classified into a particle size of 150 micrometers or less, and making the mixture into a tablet. The results are shown in FIG. 6 (the first solution: buffer solution pH 1.2) and FIG. 7 (the second solution: buffer solution pH 6.8).

The conditions for the high speed liquid chromatography measurement are as follows:

Determination of noscapine-HCl:

Detection: UV (220 nm)
Flow rate: 1.0 ml/min
Moving layer: water/acetonitrile=70/30, pH=2.2
Column: CAPCELL PAK C18 (SG120) (manufactured by Shiseido)

Determination of indomethacin:

Detection: UV (254 nm)
Flow rate: 1.0 ml/min
Moving layer: water/acetonitrile=50/50, pH=2.2
Column: CAPCELL PAK C18 (SG120) (manufactured by Shiseido)

The controlled release preparation containing a poly-ion complex of hyaluronic acid and a cationic polyacrylic acid derivative(s) according to the present invention is easy to prepare, and has a superior controlled release action which allows for adjustment of the release starting time and the duration of the release.

What is claimed is:

1. A composition comprising a poly-ion complex of hyaluronic acid and a cationic polyacrylic acid copolymer having the formula:

wherein R=CH$_3$ or C$_4$H$_9$.

2. A carrier for a bioactive substance comprising the composition of claim 1.

3. A controlled release preparation comprising a bioactive substance and a Carrier therefor of the composition of claim 1.

4. The controlled release preparation of claim 3, wherein the bioactive substance is noscapine-HCl.

5. The controlled release preparation of claim 3, wherein the bioactive substance is indomethacin.

6. The composition of claim 1, wherein the copolymer has a mean molecular weight of about 150,000.

7. A carrier for a bioactive substance of claim 2, wherein the copolymer has a mean molecular weight of about 150,000.

8. A controlled release preparation of claim 3, wherein said bioactive substance is selected from the group consisting of noscapine-HCl and indomethacin, and the copolymer has a mean molecular weight of about 150,000.

9. A controlled release preparation of claim 3, wherein the bioactive substance is present in an amount of from about 0.01–50 wt. %.

10. A composition comprising a poly-ion complex of hyaluronic acid and a cationic polyacrylic acid copolymer having the formula:

wherein R$_1$ is H or CH$_3$ and R$_2$ is CH$_3$ or C$_2$H$_5$. and wherein the molar ratio of the ammonium groups to the remaining neutral (meth)acrylic acid esters is 1:40.

11. A carrier for a bioactive substance comprising the composition of claim 10.

12. A controlled release preparation comprising a bioactive substance and a carrier therefor of the composition of claim 10.

13. The controlled release preparation of claim 12, wherein the bioactive substance is noscapine-HCl.

14. The controlled release preparation of claim 12, wherein the bioactive substance is indomethacin.

15. The composition of claim 10, wherein the copolymer has a mean molecular weight of about 150,000.

16. A carrier for a bioactive substance of claim 11, wherein the copolymer has a mean molecular weight of about 150,000.

17. A controlled release preparation of claim 10, wherein said bioactive substance is selected from the group consisting of noscapine-HCl and indomethacin, and the copolymer has a mean molecular weight of about 150,000.

18. A controlled release preparation of claim 12, wherein the bioactive substance is present in an amount of from about 0.01–50 wt. %.

* * * * *